United States Patent
Radcliffe, Jr.

(10) Patent No.: US 10,322,247 B1
(45) Date of Patent: Jun. 18, 2019

(54) INTRAVENOUS THERAPY TUBING CONNECTION SYSTEM

(71) Applicant: John C. Radcliffe, Jr., Cuba, AL (US)

(72) Inventor: John C. Radcliffe, Jr., Cuba, AL (US)

(*) Notice: Subject to any disclaimer, the term of this patent is extended or adjusted under 35 U.S.C. 154(b) by 930 days.

(21) Appl. No.: 14/872,503

(22) Filed: Oct. 1, 2015

(51) Int. Cl.
*A61M 5/34* (2006.01)
*A61M 39/10* (2006.01)
*A61M 5/14* (2006.01)
*A61M 5/32* (2006.01)
*A61M 5/31* (2006.01)
*A61M 5/178* (2006.01)

(52) U.S. Cl.
CPC .......... *A61M 5/348* (2013.01); *A61M 5/1413* (2013.01); *A61M 5/178* (2013.01); *A61M 5/3134* (2013.01); *A61M 5/3293* (2013.01); *A61M 5/34* (2013.01); *A61M 39/1055* (2013.01); *A61M 2005/3103* (2013.01); *A61M 2005/3107* (2013.01); *A61M 2005/3142* (2013.01); *A61M 2039/1027* (2013.01); *A61M 2039/1033* (2013.01)

(58) Field of Classification Search
CPC ...... A61M 5/14; A61M 5/1413; A61M 5/158; A61M 5/162; A61M 5/178; A61M 5/3134; A61M 5/32; A61M 5/3293; A61M 5/34; A61M 5/344; A61M 5/345; A61M 5/346; A61M 5/347; A61M 5/348; A61M 2005/1587; A61M 2005/3103; A61M 2005/3107; A61M 2005/3131; A61M 2005/3142; A61M 39/10; A61M 39/1011; A61M 39/1055; A61M 2039/1027; A61M 2039/1033; A61M 2039/1077

See application file for complete search history.

(56) References Cited

U.S. PATENT DOCUMENTS

| | | | |
|---|---|---|---|
| 4,152,017 A | 5/1979 | Abramson | |
| 4,254,773 A | 3/1981 | Waldbillig | |
| 4,296,949 A | 10/1981 | Muetterties et al. | |
| 5,281,206 A | 1/1994 | Lopez | |
| D363,541 S | 10/1995 | Cottone et al. | |
| 5,674,201 A | 10/1997 | Steinman | |
| 7,641,620 B2 * | 1/2010 | Wingler | A61B 10/0045 600/562 |
| 8,287,517 B2 * | 10/2012 | Hanlon | A61H 9/0078 604/533 |

* cited by examiner

*Primary Examiner* — Shefali D Patel

(57) ABSTRACT

A swiveling intravenous therapy tubing connection system for easy rotational adjustment of an intravenous tubing line between a sterile container and a catheter used to administer a fluid to a patient features the sterile container which is a sterile intravenous fluid container and the catheter which is an intravenous therapy catheter located in the patient. The system features a length of intravenous therapy tubing having a female quick-connect swivel tubing connector located on a tubing first end and a quick-connect double swivel tubing connector located on a tubing second end. The female quick-connect swivel tubing connector is rotationally connected to a first mated male swivel tubing connector located on an intravenous fluid outlet of the intravenous fluid container. The quick-connect double swivel tubing connector is rotationally connected to a second mated male swivel tubing connector located on an intravenous fluid inlet of the catheter. The length of intravenous therapy tubing is designed to be infinitely rotatable in either direction.

15 Claims, 6 Drawing Sheets

INTRAVENOUS THERAPY TUBING CONNECTION SYSTEM

FIELD OF THE INVENTION

The present invention relates to tubing, tube fittings, and other medical grade equipment used in intravenous therapy.

BACKGROUND OF THE INVENTION

Intravenous therapy has been widely available since the 1950s. An overview of some general equipment used for intravenous therapy includes a short catheter inserted into a vein of a patient connected to a sterile dispensing container via tubing. Fluid is metered at a specific rate from the dispensing container to the patient. Sometimes, however, the tube can become tangled, especially as the patient moves around to get comfortable after being in one position for a long time. The present invention features a swiveling intravenous therapy tubing connection system for easy rotational adjustment of an intravenous tubing line between a sterile container and a catheter used to administer fluid to a patient. The system is designed to stop twisting and tangling of the tubing.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a swiveling intravenous therapy tubing connection system for easy rotational adjustment of an intravenous tubing line between a sterile container and a catheter used to administer fluid to a patient. In some embodiments, the system comprises a sterile intravenous fluid container having an intravenous fluid outlet located thereon.

In some embodiments, the system comprises an intravenous therapy catheter located in a patient. In some embodiments, the intravenous therapy catheter comprises an intravenous fluid inlet located thereon. In some embodiments, the system comprises a length of intravenous therapy tubing. In some embodiments, the system comprises a female quick-connect swivel tubing connector located on a tubing first end. In some embodiments, the system comprises a quick-connect double swivel tubing connector located on a tubing second end.

In some embodiments, the female quick-connect swivel tubing connector is rotationally connected to a first mated male swivel tubing connector located on the intravenous fluid outlet of the intravenous fluid container. In some embodiments, the quick-connect double swivel tubing connector is rotationally connected to a second mated male swivel tubing connector located on the intravenous fluid inlet of the catheter.

In some embodiments, the length of intravenous therapy tubing is designed to be infinitely rotatable in either direction via the female quick-connect swivel tubing connector and the quick-connect double swivel tubing connector.

BRIEF DESCRIPTION OF THE DRAWINGS

An intravenous tubing male quick connect connector is inserted into an in-line intravenous tubing female quick connect connector with a single swivel. The present invention helps keep intravenous tubing from twisting, kinking, and tangling and comes made into intravenous tubing from the factory. A new type of intravenous tubing and intravenous swivel with quick connector is represented.

DESCRIPTION OF PREFERRED EMBODIMENTS

Figure 1:
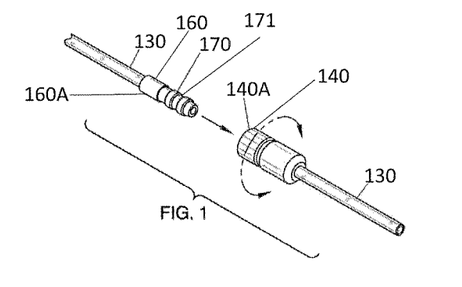
FIG. 1 shows an in-line intravenous tubing quick-connect connector with a single swivel (with male and female ends).
Figure 2A:
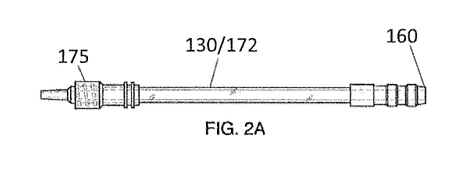
FIG. 2A and FIG. 2B shows a standard intravenous connector female end combined with a quick connect connector male end. The present invention therefore enables one to use an existing intravenous hook-up with the new quick connect connectors. The present invention thus makes it easier to phase-out existing intravenous connectors and phase-in the new intravenous connectors of the present invention.
Figure 2B:
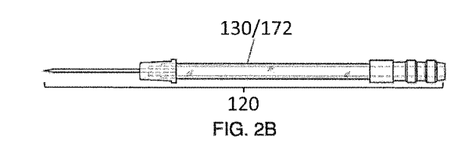
Figure 3:
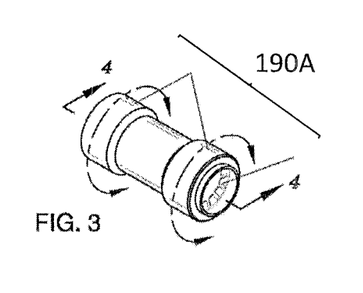
FIG. 3 shows an in-line intravenous tubing double swivel and a self-sealing and self-locking quick connector. The present invention enables one to use additional swivels to help prevent twisting, kinking, and tangling of intravenous tubing. It can be used on existing intravenous tubing, and on new intravenous tubing. One simply inserts intravenous tubing into each end of the double swivel until the tubing bottoms out. The present invention thus quickly and easily hooks up to intravenous tubing.
Figure 4:
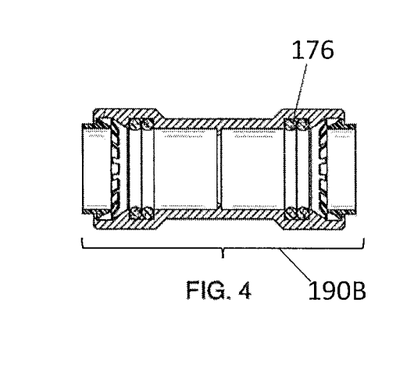
FIG. 4 shows an in-line intravenous tubing double swivel quick connector. This view enables one to see the internal parts of the double swivel quick connector.
Figure 5:
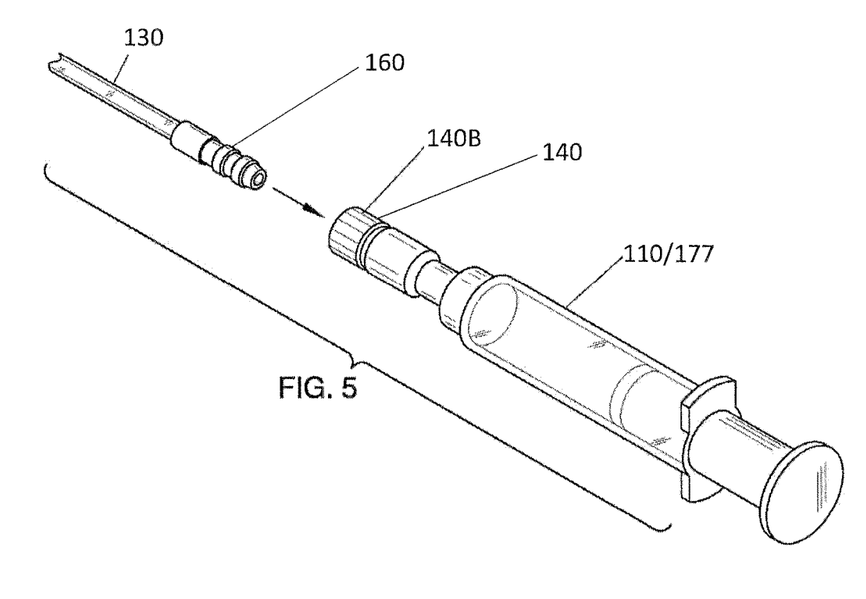
FIG. 5 shows in-line intravenous tubing with a male quick connect to female quick connect syringe. The syringe quick connect female end is always non-swivel on the syringe only. The syringe female end is self-sealing until the male end quick connector is inserted into the female end, at which point fluid easily flows outward when it is administered via the operation of the plunger of the syringe in an ordinary manner. The present invention makes hook-up easy and fast.
Figure 6:
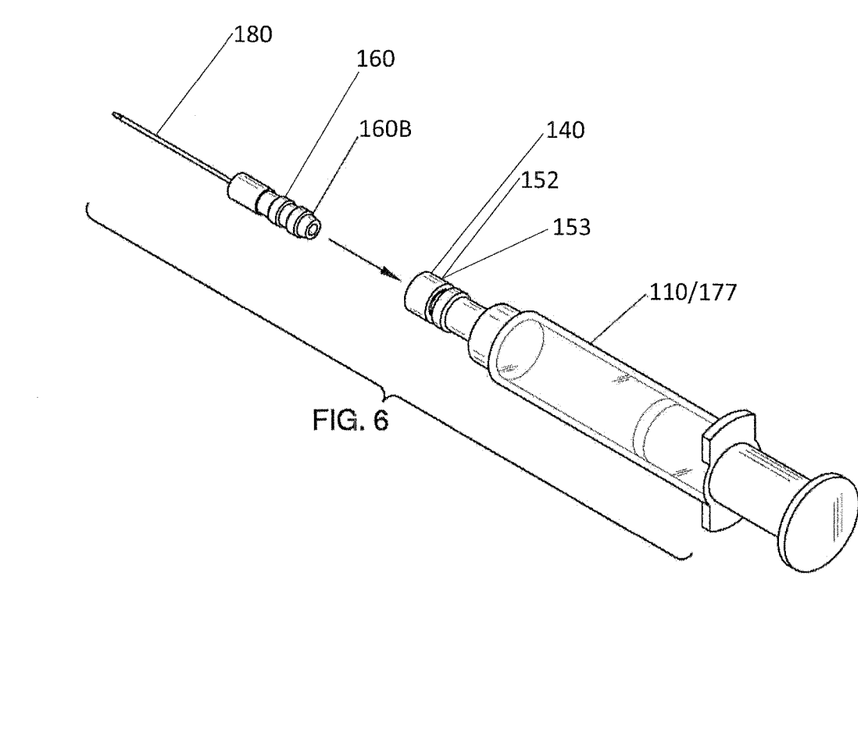
FIG. 6 shows a needle with a quick connect male end to quick connect female end of a syringe. The quick connect male end of the needle and the quick connect female end of the syringe are self-sealing and self-locking once placed together. The present invention makes hook-up easy and fast. The female end of the syringe does not swivel.
Figure 7A:
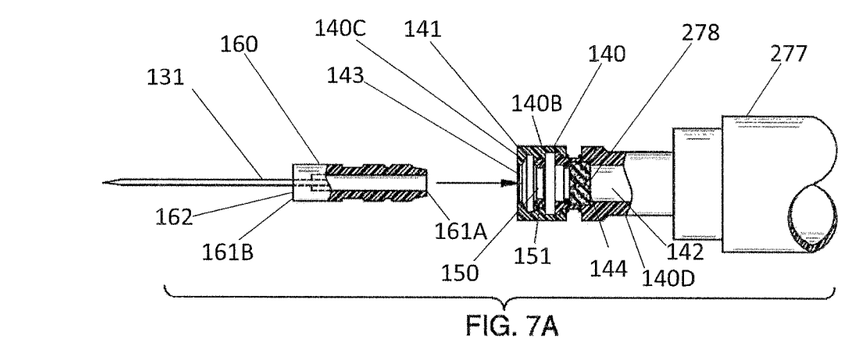
FIG. 7A shows a needle with a quick connect male end to a quick connect female end of a syringe. The internal parts are un-connected.
Figure 7B:
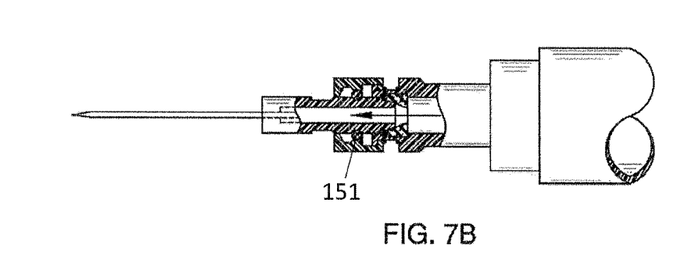
FIG. 7B shows a needle with a quick connect male end to a quick connect female end of a syringe. The internal parts are connected.
Figure 8:
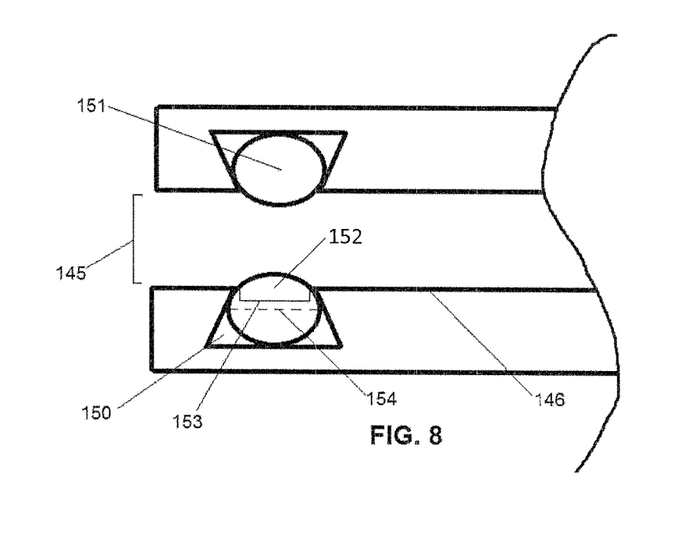
FIG. 8 shows a close up view of the sealing o-ring of the present invention.

Following is a list of elements corresponding to a particular element referred to herein:
- 110 Syringe Fluid Container
- 120 Intravenous therapy catheter with a quick connect male end
- 130 Intravenous tubing
- 131 Tubing first end
- 140 Female quick connect swivel tubing connector
- 140A In-line single female end swivel quick connector
- 140B Syringe non-swivel female end quick connector
- 140C Female quick connect swivel tubing connector first end
- 140D Female quick connect swivel tubing connector second end 141 Front of syringe outlet body
142 Syringe internal inlet
143 First opening of internal channel
144 Second opening of internal channel
145 Interior channel
146 Interior channel wall
150 Annular indentation
151 Sealing o-ring
152 Indentation o-ring opening
153 Width of indentation o-ring opening
154 Annular sealing o-ring width
160 Male swivel tubing connector
160A Part of male end quick connector that intravenous tubing is made into
160B Front of intravenous tubing male end quick connector
161A Male swivel tubing connector first end
161B Male swivel tubing connector second end
162 Part of male end quick connector that syringe needle is made into
170 Ring on male end of intravenous quick connector (annular ridge)
171 Groove on male end of intravenous quick connector (annular groove)
172 Intravenous tubing that is between the standard intravenous female connector that connects the old, standard intravenous fitting with the new intravenous quick connector fitting on the other end of tubing
175 Standard intravenous female connector (adapter component)
176 Cross section of sealing o-ring (internal view)
177 Syringe
180 Needle
190A In-line double, non-directional, self-sealing, self-locking swivel quick
190B Cross section of in-line double, non-directional, self-sealing, self-locking swivel quick connector (internal view)
277 A part belonging to a syringe (177), a medical dispenser
278 Internal outlet portal Referring now to FIG. 1-8, the present invention features a swiveling intravenous therapy tubing connection system for easy rotational adjustment of an intravenous line between a sterile container and a catheter used to administer fluid to a patient. In some embodiments, the system comprises a sterile intravenous fluid container (110) having an intravenous fluid outlet located thereon. Sterile intravenous fluid containers (110) are well known to those of ordinary skill in the art. In some embodiments, the intravenous fluid outlet comprises a length of tubing fluidly connected to an inside of the intravenous fluid container (110).

In some embodiments, the system comprises an intravenous therapy catheter located in a vein of a patient. In some embodiments, the intravenous therapy catheter comprises an intravenous fluid inlet located thereon. Intravenous therapy catheters (120) are well known to those of ordinary skill in the art.

In some embodiments, the system comprises a length of intravenous therapy tubing (130) having a tubing first end and a tubing second end. In some embodiments, the system comprises a female quick-connect swivel tubing connector (140) permanently located on the tubing first end. In some embodiments, the system comprises a quick-connect double swivel tubing connector (190) permanently located on the tubing second end. Quick-connect male swivel tubing connectors are well known to those of ordinary skill in the art.

In some embodiments, the female quick-connect swivel tubing connector (140) is rotationally and removably connected to a first mated male swivel tubing connector (160) permanently located on the intravenous fluid outlet of the intravenous fluid container (110). In some embodiments, the quick-connect double swivel tubing connector (190) is rotationally and removably connected to a second mated male swivel tubing connector (160) permanently located on the intravenous fluid inlet of the intravenous therapy catheter. In some embodiments, the intravenous fluid container (110) is fluidly connected to the intravenous therapy catheter via the length of intravenous therapy tubing (130).

In some embodiments, the length of intravenous therapy tubing (130) is cut in half for permanent insertion of the female quick-connect swivel tubing connector (140) without the use of a male swivel tubing connector (160). In some embodiments, the length of intravenous therapy tubing (130) is cut in half for permanent insertion of the quick-connect double swivel tubing connector (190) without the use of a male swivel tubing connector (160). In some embodiments, the female quick-connect swivel tubing connector (140) and the quick-connect double swivel tubing connector (190) are push-to-connect fittings.

In some embodiments, the length of intravenous therapy tubing (130) is designed to be infinitely rotatable in either direction via the female quick-connect swivel tubing connector (140) and the quick-connect double swivel tubing connector (190).

In some embodiments, the mated male swivel tubing connector (160) is a stationary male connector comprising a pair of annular ridges (170) having an annular groove (171) located in between the pair of annular ridges (170).

In some embodiments, the system comprises an adapter component (172). In some embodiments, the adapter component (172) comprises a second length of intravenous therapy tubing (130). In some embodiments, the adapter component (172) comprises the mated male swivel tubing connector (160) permanently located on an adapter first end and a standard intravenous therapy tubing connector (175) permanently located on an adapter second end. In some embodiments, the adapter component (172) is designed to adapt standard intravenous therapy tubing to utilize the intravenous therapy tubing connection system.

In some embodiments, the female quick-connect swivel tubing connector (140) and the quick-connect double swivel tubing connector (190) each comprise two sealing o-rings (151) located on each end of the connector therein.

In some embodiments, the female quick-connect swivel tubing connector (140) and the quick-connect double swivel tubing connector (190) are push-to-connect fittings.

In some embodiments, the sterile intravenous fluid container (110) is a syringe (177).

In some embodiments, the sterile intravenous fluid container (110) is an intravenous fluid bag.

In some embodiments, the male swivel tubing connector (160) comprises a needle point designed to sealably push into a receiving seal of the source quick-connect tubing connector (140) or the quick-connect double swivel tubing connector (190).

The present invention features a swiveling intravenous therapy tubing connection system for easy rotational adjustment of an intravenous line between a sterile container and a catheter used to administer fluid to a patient. In some embodiments, the system comprises a sterile intravenous fluid container (110) having an intravenous fluid outlet located thereon.

In some embodiments, the system comprises an intravenous therapy catheter located in a vein of a patient. In some embodiments, the intravenous therapy catheter comprises an intravenous fluid inlet located thereon.

In some embodiments, the system comprises a length of intravenous therapy tubing (130) having a tubing first end and a tubing second end.

In some embodiments, the system comprises a female quick-connect swivel tubing connector (140) located on the tubing first end or the intravenous fluid outlet.

In some embodiments, the tubing second end is disposed on the intravenous fluid inlet.

In some embodiments, the system comprises a male swivel tubing connector (160) located on a mated tubing first end or the intravenous fluid outlet. In some embodiments, the female quick-connect swivel tubing connector (140) is rotationally connected to a first mated male swivel tubing connector (160).

In some embodiments, the intravenous fluid container (110) is fluidly connected to the intravenous therapy catheter via the length of intravenous therapy tubing (130).

In some embodiments, the length of intravenous therapy tubing (130) is designed to be infinitely rotatable in either direction via the female quick-connect swivel tubing connector (140) and the quick-connect double swivel tubing connector (190).

In some embodiments, the system further comprises a quick-connect double swivel tubing connector (190) rotationally located in the intravenous therapy tubing (130). In some embodiments, the quick-connect double swivel tubing connector (190) is inserted in a middle of the intravenous therapy tubing (130) to provide a swivel for easy rotation of the intravenous therapy tubing (130).

In some embodiments, the mated male swivel tubing connector (160) is a stationary male connector comprising a pair of annular ridges (170) having an annular groove (171) located in between the pair of annular ridges (170).

In some embodiments, the system comprises an adapter component (172). In some embodiments, the adapter component (172) comprises the mated male swivel tubing connector (160) located on an adapter first end and a standard intravenous therapy tubing connector (175) located on an adapter second end. In some embodiments, the adapter component (172) is designed to adapt standard intravenous therapy tubing to utilize the intravenous therapy tubing connection system.

In some embodiments, the female quick-connect swivel tubing connector (140) and the quick-connect double swivel tubing connector (190) each comprise two sealing o-rings (151) located on each end of the connector therein.

In some embodiments, the female quick-connect swivel tubing connector (140) and the quick-connect double swivel tubing connector (190) are push-to-connect fittings.

In some embodiments, the sterile intravenous fluid container (110) is an intravenous fluid bag.

In some embodiments, the system further comprises a syringe (177) having an intravenous fluid outlet located thereon, a needle (180), a source quick-connect non-male swivel tubing connector located on the fluid outlet of the syringe (177), and a connector located on the needle (180).

In some embodiments, the connector is connected to the source quick-connect non-male swivel tubing connector located on the intravenous fluid outlet of the syringe (177). In some embodiments, the syringe (177) is fluidly connected to the needle (180) via the source quick-connect non-male swivel tubing connector and the connector.

In some embodiments, the present invention features a swiveling intravenous therapy tubing connection system for easy rotational adjustment of an intravenous line between a sterile container and a catheter used to administer fluid to a patient. In some embodiments, the system comprises a sterile intravenous fluid container (110) having an intravenous fluid outlet located thereon. In some embodiments, the fluid container (110) is a syringe (177).

In some embodiments, the system comprises a needle (180).

In some embodiments, the system comprises a source quick-connect non-male swivel tubing connector located on a fluid outlet of the syringe (177).

In some embodiments, the system comprises a connector located on the needle (180).

In some embodiments, the connector is connected to the source quick-connect non-male swivel tubing connector located on the intravenous fluid outlet of the intravenous fluid container (110). In some embodiments, the intravenous fluid container (110) is fluidly connected to the needle (180) via the source quick-connect non-male swivel tubing connector and the connector.

A method of preventing twisting in intravenous tubing applications consists of obtaining an intravenous therapy tubing connection system consisting of a sterile intravenous fluid container (110), a length of intravenous therapy tubing (130) fluidly connected to an intravenous therapy catheter, or a needle (180), a female quick-connect swivel tubing connector (140), and a male swivel tubing connector (160).

A method of preventing twisting in intravenous tubing applications consists of fluidly connecting the fluid container (110) to the length of intravenous therapy tubing (130), or the needle (180) via fluidly connecting the female quick-connect swivel tubing connector (140) to an outlet of the fluid container (110), and fluidly connecting the male swivel tubing connector (160) to the length of intravenous therapy tubing (130), or the needle (180).

In some embodiments, the system designed to be infinitely rotatable in either direction via the female quick-connect swivel tubing connector (140) and the male swivel tubing connector (160).

In some embodiments, the method consists of obtaining an adapter component (172). In some embodiments, the adapter component consists of a standard intravenous therapy tubing connector (175) located on and fluidly connected to a first tube end and either a female quick-connect swivel tubing connector (140) or a male swivel tubing connector (160) located on and fluidly connected to a second tube end.

In some embodiments, the method consists of fluidly connecting the standard intravenous therapy tubing connector (175) of the adapter component (172) to mated standard intravenous therapy tubing connections.

In some embodiments, the method consists of fluidly connecting the female quick-connect swivel tubing connector (140) or the male swivel tubing connector (160) of the adapter component (172) to swivel tubing connections.

In some embodiments, the adapter component (172) adapts the intravenous therapy tubing swivel connection system to a traditional intravenous therapy tubing connection system.

In some embodiments, the method consists of obtaining a quick-connect double swivel tubing connector (190). In some embodiments, the method consists of disposing and fluidly connecting the quick-connect double swivel tubing connector (190) to the length of intravenous therapy tubing.

In some embodiments, the quick-connect double swivel tubing connector (190) is inserted in the length of intravenous therapy tubing (130) to provide a swivel for easy rotation of the intravenous therapy tubing (130).

In some embodiments, the mated male swivel tubing connector (160) is a stationary male connector consisting of a pair of annular ridges (170) having an annular groove (171) located in between the pair of annular ridges (170).

In some embodiments, the female quick-connect swivel tubing connector (140) and the quick-connect double swivel tubing connector (190) each consists of two sealing o-rings (151) located on each end of the connector therein.

In some embodiments, the female quick-connect swivel tubing connector (140) and the quick-connect double swivel tubing connector (190) are push-to-connect fittings.

In some embodiments, the sterile intravenous fluid container (110) is an intravenous fluid bag.

In some embodiments, a method of preventing twisting in intravenous tubing applications comprises obtaining an intravenous therapy tubing connection system comprising a sterile intravenous fluid container (110), a length of intravenous therapy tubing (130) fluidly connected to an intravenous therapy catheter, or a needle (180), a female quick-connect swivel tubing connector (140), and a male swivel tubing connector (160).

In some embodiments, a method of preventing twisting in intravenous tubing applications comprises fluidly connecting the fluid container (110) to the length of intravenous therapy tubing (130), or the needle (180) via fluidly connecting the female quick-connect swivel tubing connector (140) to an outlet of the fluid container (110), and fluidly connecting the male swivel tubing connector (160) to the length of intravenous therapy tubing (130), or the needle (180).

In some embodiments, the system designed to be infinitely rotatable in either direction via the female quick-connect swivel tubing connector (140) and the male swivel tubing connector (160).

In some embodiments, a method of preventing twisting in intravenous tubing applications further comprises obtaining an adapter component (172). In some embodiments, the adapter component comprises a standard intravenous therapy tubing connector (175) located on and fluidly connected to a first tube end and either a female quick-connect swivel tubing connector (140) or a male swivel tubing connector (160) located on and fluidly connected to a second tube end.

In some embodiments, a method of preventing twisting in intravenous tubing applications comprises fluidly connecting the standard intravenous therapy tubing connector (175) of the adapter component (172) to mated standard intravenous therapy tubing connections.

In some embodiments, a method of preventing twisting in intravenous tubing applications comprises fluidly connecting the female quick-connect swivel tubing connector (140) or the male swivel tubing connector (160) of the adapter component (172) to swivel tubing connections.

In some embodiments, the adapter component (172) adapts the intravenous therapy tubing swivel connection system to a traditional intravenous therapy tubing connection system.

In some embodiments, a method of preventing twisting in intravenous tubing applications comprises obtaining an intravenous therapy tubing connection system comprising a sterile intravenous fluid container (110), a length of intravenous therapy tubing (130) fluidly connected to an intravenous therapy catheter, or a needle (180), a female quick-connect swivel tubing connector (140), and a male swivel tubing connector (160).

In some embodiments, a method of preventing twisting in intravenous tubing applications comprises obtaining an adapter component (172). In some embodiments, the adapter component comprises a standard intravenous therapy tubing connector (175) located on and fluidly connected to a first tube end and either a female quick-connect swivel tubing connector (140) or a male swivel tubing connector (160) located on and fluidly connected to a second tube end. In some embodiments, the adapter component (172) adapts the intravenous therapy tubing swivel connection system to a traditional intravenous therapy tubing connection system.

In some embodiments, a method of preventing twisting in intravenous tubing applications comprises fluidly connecting the fluid container (110) to the length of intravenous therapy tubing (130), or the needle (180) via fluidly connecting the female quick-connect swivel tubing connector (140) to an outlet of the fluid container (110), and fluidly connecting the male swivel tubing connector (160) to the length of intravenous therapy tubing (130), or the needle (180).

In some embodiments, a method of preventing twisting in intravenous tubing applications comprises fluidly connecting the standard intravenous therapy tubing connector (175) of the adapter component (172) to mated standard intravenous therapy tubing connections.

In some embodiments, a method of preventing twisting in intravenous tubing applications comprises fluidly connecting the female quick-connect swivel tubing connector (140) or the male swivel tubing connector (160) of the adapter component (172) to swivel tubing connections.

In some embodiments, the system is designed to be infinitely rotatable in either direction via the female quick-connect swivel tubing connector (140) and the male swivel tubing connector (160).

As used herein, the term "about" refers to plus or minus 10% of the referenced number.

The disclosures of the following U.S. Patents are incorporated in their entirety by reference herein: U.S. Pat. No. D 363,541; U.S. Pat. Nos. 5,674,201; 5,281,206; 4,296,949; 4,254,773; and 4,152,017.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system for intravenous administration comprising:
    a) a medical dispenser (277) having an outlet portal (278) fitted with a female quick-connect swivel tubing connector (140), the female quick-connect swivel tubing connector comprising:
        i. a female quick-connect swivel tubing connector first end (141);
        ii. a female quick-connect swivel tubing connector second end (142);
        iii. a first opening (143) disposed on the female quick-connect swivel tubing connector first end (141);
        iv. a second opening (144) disposed on the female quick-connect swivel tubing connector second end (142);
        v. an interior channel (145) formed by an interior channel wall (146) fluidly connecting the first opening (143) and the second opening (144);
        vi. an annular indentation (150) disposed inside the interior channel wall (146); and
        vii. a sealing o-ring (151) disposed in the annular indentation (150), wherein the annular indentation (150) has an indentation o-ring opening (152) having a width (153) smaller than an annular sealing o-ring width (154) of the sealing o-ring (151) such that the sealing o-ring is confined within the annular indentation, wherein the sealing o-ring (151) held within the interior channel wall (146) is disposed such that the sealing o-ring (151) protrudes partially from the interior channel wall (146) and into the interior channel (145); and
    b) an intravenous tubing (130) having a tubing first end (131) fitted with a male swivel tubing connector (160), the male swivel tubing connector (160) comprising:
        i. a male swivel tubing connector first end (161A);
        ii. a male swivel tubing connector second end (161B); and
        iii. an annular groove (171) disposed on an exterior surface of the male swivel tubing connector (160) between the male swivel tubing connector first end (161A) and the male swivel tubing connector second end (161B);
    wherein the intravenous tubing (130) is free of twists and crimps;
    wherein when the system is in use, the male swivel tubing connector first end (161A) mateably slides into the first opening (143) of the female quick-connect swivel tubing connector (140) such that the male swivel tubing connector (160) is slidably fitted into the interior channel (145) of the female quick-connect swivel tubing connector (140), wherein the protruding sealing o-ring (151) mateably fits into the annular groove (171) such that the male swivel tubing connector (160) is rotatable within the female quick-connect swivel tubing connector (140).

2. The system of claim 1, wherein the male swivel tubing connector (160) further comprises a hollow male swivel tubing connector interior channel fluidly connecting the male swivel tubing connector first end (161A) and the male swivel tubing connector second end (161B).

3. The system of claim 1, wherein a needle is disposed on the intravenous tubing (130) at a tubing second end, and opposite the male swivel tubing connector (160).

4. The system of claim 1, wherein the medical dispenser (277) is a syringe.

5. The system of claim 1, wherein the medical dispenser (277) is an intravenous fluid bag.

6. The system of claim 1, wherein a sealing o-ring (151) is disposed on the female quick-connect swivel tubing connector first end (141).

7. The system of claim 1, wherein a sealing o-ring (151) is disposed on the male swivel tubing connector first end (440D) (161A).

8. The system of claim 1, wherein the female quick-connect swivel tubing connector (140) and the male swivel tubing connector (160) are push-to-connect fittings.

9. A syringe for intravenous administration comprising:
    a) a female quick-connect swivel tubing connector (140) disposed on a syringe first end, the female quick-connect swivel tubing connector comprising:
        i. a female quick-connect swivel tubing connector first end (140C);
        ii. a female quick-connect swivel tubing connector second end (140D), wherein the female quick-connect swivel tubing connector second end (140D) is fluidly connected to the syringe first end;
        iii. a first opening (143) disposed on the female quick-connect swivel tubing connector first end (140C);
        iv. a second opening (144) disposed on the female quick-connect swivel tubing connector second end (140D);
        v. an interior channel (145) formed by an interior channel wall (146) fluidly connecting the first opening (143) and the second opening (144);
        vi. an annular indentation (150) disposed inside the interior channel wall (146); and
        vii. a sealing o-ring (151) disposed in the annular indentation (150), wherein the annular indentation (150) has an indentation o-ring opening (152) having a width (153) smaller than an annular sealing o-ring width (154) of the sealing o-ring (151) such that the sealing o-ring is confined within the annular indentation, wherein the sealing o-ring (151) held within the interior channel wall (146) is disposed such that the sealing o-ring (151) protrudes partially from the interior channel wall (146) and into the interior channel (145); and
    b) a male swivel tubing connector (160), the male swivel tubing connector comprising:
        i. a male swivel tubing connector first end (161A);
        ii. a male swivel tubing connector second end (161B); and
        iii. an annular groove (171) disposed on an exterior surface of the male swivel tubing connector (160) between the male swivel tubing connector first end (161A) and the male swivel tubing connector second end (161B);
    wherein the male swivel tubing connector first end (161A) mateably slides into the first opening (143) of the female quick-connect swivel tubing connector (140) such that the male swivel tubing connector (160) is slidably fitted into the interior channel (145) of the female quick-connect swivel tubing connector (140), wherein the protruding sealing o-ring (151) mateably fits into the annular groove (171) such that the male swivel tubing connector (160) is rotatable within the female quick-connect swivel tubing connector (140).

10. The system of claim 9, wherein the male swivel tubing connector (160) further comprises a hollow male swivel tubing connector interior channel fluidly connecting the male swivel tubing connector first end (161A) and the male swivel tubing connector second end (161B).

11. The system of claim 9, wherein a needle is disposed at the male swivel tubing connector second end (161B).

12. The system of claim 9, wherein a sealing o-ring (151) is disposed on the female quick-connect swivel tubing connector first end (140C).

13. The system of claim 9, wherein a sealing o-ring (151) is disposed on the male swivel tubing connector first end (161A).

14. The system of claim 9, wherein the female quick-connect swivel tubing connector (140) and the male swivel tubing connector (160) are push-to-connect fittings.

15. A syringe for intravenous administration consisting of:
a) a female quick-connect swivel tubing connector (140) disposed on a syringe first end, the female quick-connect swivel tubing connector consisting of:
 i. a female quick-connect swivel tubing connector first end (140C);
 ii. a female quick-connect swivel tubing connector second end (140D), wherein the female quick-connect swivel tubing connector second end (140D) is fluidly connected to the syringe first end;
 iii. a first opening (143) disposed on the female quick-connect swivel tubing connector first end (140C);
 iv. a second opening (144) disposed on the female quick-connect swivel tubing connector second end (140D);
 v. an interior channel (145) formed by an interior channel wall (146) fluidly connecting the first opening (143) and the second opening (144);
 vi. an annular indentation (150) disposed inside the interior channel wall (146); and
 vii. a sealing o-ring (151) disposed in the annular indentation (150), wherein the annular indentation (150) has an indentation o-ring opening (152) having a width (153) smaller than an annular sealing o-ring width (154) of the sealing o-ring (151) such that the sealing o-ring is confined within the annular indentation, wherein the sealing o-ring (151) held within the interior channel wall (146) is disposed such that the sealing o-ring (151) protrudes partially from the interior channel wall (146) and into the interior channel (145); and
b) a male swivel tubing connector (160), the male swivel tubing connector consisting of:
 i. a male swivel tubing connector first end (161A);
 ii. a male swivel tubing connector second end (161B);
 iii. an annular groove (171) disposed on an exterior surface of the male swivel tubing connector (160) between the male swivel tubing connector first end (161A) and the male swivel tubing connector second end (161B); and
 iv. a hollow male swivel tubing connector interior channel fluidly connecting the male swivel tubing connector first end (161A) and the male swivel tubing connector second end (161B);
wherein the male swivel tubing connector first end (161A) mateably slides into the first opening (143) of the female quick-connect swivel tubing connector (140) such that the male swivel tubing connector (160) is slidably fitted into the interior channel (145) of the female quick-connect swivel tubing connector (140), wherein the protruding sealing o-ring (151) mateably fits into the annular groove (171) such that the male swivel tubing connector (160) is rotatable within the female quick-connect swivel tubing connector (140).

* * * * *